(12) United States Patent
Mohammadkhah et al.

(10) Patent No.: US 10,590,031 B2
(45) Date of Patent: Mar. 17, 2020

(54) METHOD AND SYSTEM UTILIZING ELLIPSOMETRY TO DETECT CORROSION ON GLASS

(71) Applicant: Guardian Glass, LLC, Auburn Hills, MI (US)

(72) Inventors: Ali Mohammadkhah, Auburn Hills, MI (US); Shuang Ji, Auburn Hills, MI (US); Jay Riggins, Auburn Hills, MI (US); Kevin R. Fulton, Howell, MI (US)

(73) Assignee: GUARDIAN GLASS, LLC, Auburn Hills, MI (US)

( * ) Notice: Subject to any disclaimer, the term of this patent is extended or adjusted under 35 U.S.C. 154(b) by 1 day.

(21) Appl. No.: 15/977,039

(22) Filed: May 11, 2018

(65) Prior Publication Data

US 2019/0345057 A1    Nov. 14, 2019

(51) Int. Cl.
| | |
|---|---|
| *G01N 21/86* | (2006.01) |
| *C03C 17/00* | (2006.01) |
| *G01N 21/21* | (2006.01) |
| *G01N 33/38* | (2006.01) |

(52) U.S. Cl.
CPC .......... *C03C 17/001* (2013.01); *G01N 21/211* (2013.01); *G01N 21/86* (2013.01); *G01N 33/386* (2013.01); *C03C 2217/70* (2013.01); *C03C 2218/154* (2013.01); *G01N 2021/8654* (2013.01)

(58) Field of Classification Search
CPC .... G01N 21/211; G01N 33/386; G01N 21/86; C03C 17/001; C03C 2217/70; C03C 2218/154
See application file for complete search history.

(56) References Cited

U.S. PATENT DOCUMENTS

| | | |
|---|---|---|
| 5,214,008 A | 5/1993 | Beckwith et al. |
| 5,344,718 A | 9/1994 | Hartig et al. |
| 5,557,462 A | 9/1996 | Hartig et al. |

(Continued)

FOREIGN PATENT DOCUMENTS

| | | |
|---|---|---|
| CN | 106501279 A | 3/2017 |
| KR | 2016-0005160 A | 1/2016 |

OTHER PUBLICATIONS

Anju Sharma, "Role of surface defects on the corrosion behavior of commercial soda-lime silicate glasses", 2002 (Year: 2002).*

(Continued)

*Primary Examiner* — Maurice C Smith (57) ABSTRACT

An ellipsometry system detects and/or identifies significant corrosion on glass, such as on soda-lime-silica based float glass. In certain example embodiments, there is provided a method and/or system using ellipsometry to detect and/or identify significant corrosion on soda-lime-silica based glass, so that such significantly corroded glass can be identified and not coated with a low-E coating and/or not used in applications where optical appearance is important. The ellipsometry system may be part of, or used in connection with, a sputtering apparatus/system for sputter-depositing low-E coatings on glass, so that whether to pass a piece of glass to the sputtering apparatus/system is based on whether significant corrosion is detected on the glass.

30 Claims, 7 Drawing Sheets

Relation between Polarization Change and Ellipsometric Parameters ($\Delta$, $\Psi$)

$$\Delta = \Delta_p - \Delta_s$$

$$\tan \Psi = \frac{(E_p/E_s)\text{Reflected}}{(E_p/E_s)\text{Incident}}$$

$$\frac{r_p}{r_s} = \tan\Psi \, e^{i\Delta}$$

(56) References Cited

U.S. PATENT DOCUMENTS

| | | | | |
|---|---|---|---|---|
| 6,132,881 | A * | 10/2000 | Hartig | C03C 17/36 359/360 |
| 6,576,349 | B2 | 6/2003 | Lingle et al. | |
| 6,597,463 | B1 * | 7/2003 | Singh | G01B 11/0625 356/364 |
| 6,660,651 | B1 * | 12/2003 | Markle | H01L 21/67259 156/345.24 |
| 6,927,186 | B2 | 8/2005 | Hulme et al. | |
| 6,947,805 | B1 * | 9/2005 | Castle | G05B 19/41865 700/108 |
| 6,953,759 | B2 | 10/2005 | Landa et al. | |
| 7,106,425 | B1 * | 9/2006 | Bultman | G01N 21/211 356/237.2 |
| 7,153,579 | B2 | 12/2006 | Kriltz et al. | |
| 7,268,876 | B1 * | 9/2007 | Johs | G01N 21/211 250/559.09 |
| 7,390,572 | B2 | 6/2008 | Butz et al. | |
| 7,560,402 | B2 | 7/2009 | Thomsen et al. | |
| 7,601,660 | B2 | 10/2009 | Tullman et al. | |
| 7,858,545 | B2 | 12/2010 | Landa et al. | |
| 8,669,197 | B2 | 3/2014 | Broughton et al. | |
| 9,212,417 | B2 | 12/2015 | Frank et al. | |
| 9,297,197 | B2 | 3/2016 | Lao et al. | |
| 9,403,345 | B2 | 8/2016 | Lao et al. | |
| 2002/0064662 | A1 | 5/2002 | Lingle et al. | |
| 2017/0176323 | A1 * | 6/2017 | Murayama | G01N 21/21 |
| 2018/0073979 | A1 * | 3/2018 | Cho | G01N 21/211 |

OTHER PUBLICATIONS

Kaspara, et at, "Non-destructive characterization of corroded glass surfaces by spectroscopic ellipsometry", Journal pf Non-Crystalline Solids, vol. 481, pp. 260-266, 2018.

Tsuchihashi, et al., "Chemical attack of optical glass surface by formic acid vapor", Journal of Non-Crystalline Solids, vol. 19, pp. 221-239, Dec. 1975. (Abstract).

Sakata, et al., "Ellipsometry-like analysis of polarization state for micro cracks using stress-induced light scattering method", SPIE, vol. 9754, pp. 97541C-97541C, 2016. (Abstract).

International Search Report and Written Opinion received for PCT application No. PCT/IB2019/053879, dated Aug. 27, 2019, 19 pages.

* cited by examiner

METHOD AND SYSTEM UTILIZING ELLIPSOMETRY TO DETECT CORROSION ON GLASS

This application relates to a method and/or system utilizing ellipsometry to detect and/or identify significant corrosion on glass. In certain example embodiments, there is provided a method and/or system using ellipsometry to detect and/or identify significant corrosion on soda-lime-silica based glass, so that such significantly corroded glass can be identified and not coated with a low-E coating and/or not used in other applications where optical appearance is important.

BACKGROUND AND SUMMARY OF THE INVENTION

Coated articles are known in the art for use in window applications such as insulating glass (IG) window units, vehicle windows, monolithic windows, and/or the like. Such window applications may involve soda-lime-silica based glass coated with coatings such as low emissivity (low-E) coatings. Example soda-lime-silica based glasses are described, for example and without limitation, in U.S. Pat. Nos. 5,214,008, 6,927,186, 6,953,759, 7,560,402, 7,601,660, 7,858,545, and 8,669,197, the disclosures of which are hereby entirely incorporated herein by reference. Low-E coatings typically include at least one infrared (IR) reflecting layer(s) sandwiched between at least first and second dielectric layer, for blocking at least some solar radiation from entering buildings, vehicles, and/or the like. Example low-E coatings are disclosed, for example and without limitation, in U.S. Pat. Nos. 6,576,349, 9,212,417, 9,297,197, 7,390,572, 7,153,579, and 9,403,345, the disclosures of which are hereby entirely incorporated herein by reference.

In certain example embodiments of this invention, there is provided a method and/or system utilizing ellipsometry to detect/identify significant corrosion (e.g., sodium carbonate, calcium carbonate, sodium sulfate, and/or sodium nitrate based corrosion, from Stage 1 and/or Stage 2 corrosion) on soda-lime-silica based glass or on other types of glass, so that such significantly corroded glass can be identified and not coated (e.g., with a low-E coating or other type of coating) and/or not used in applications where optical appearance is critical. In certain example embodiments, ellipsometry is utilized to differentiate between corroded glass and non-corroded glass, so that significantly corroded glass can be detected/identified. In certain example embodiments, the method and/or system using ellipsometry to detect and/or identify corrosion on glass may be part of, or used in conjunction with, a sputtering apparatus that sputter-deposits coatings (e.g., low-E coatings, or other types of coatings) on glass.

In an example embodiment of this invention, there is provided a method of making a coated glass sheet, the method comprising: analyzing an uncoated glass sheet via ellipsometry analysis, including directing radiation toward the uncoated glass sheet so as to be reflected by the uncoated glass sheet; determining (e.g., by at least one processor of an ellipsometry or other system) whether or not the uncoated glass sheet has significant corrosion thereon based on the ellipsometry or other analysis; and selectively allowing the uncoated glass sheet to be coated with a low-E coating (or other coating) based at least on whether significant corrosion is determined to be on the uncoated glass sheet.

The determining may comprise determining whether or not the uncoated glass sheet has significant corrosion thereon based at least on a measured delta ($\Delta$) value, wherein the measured delta ($\Delta$) value is based on at least a polarization change between the radiation incident on the uncoated glass sheet and the radiation reflected by the uncoated glass sheet. The determining may comprise determining whether or not the uncoated glass sheet has significant corrosion thereon based at least on whether the measured delta ($\Delta$) value exceeds a predetermined value, so that it is determined that the uncoated glass sheet is not significantly corroded when the measured delta ($\Delta$) value exceeds the predetermined value, and it is determined that the uncoated glass sheet is significantly corroded when the measured delta ($\Delta$) value does not exceed the predetermined value. The measured delta ($\Delta$) value may comprise at least one delta ($\Delta$) value measured for at least one wavelength from about 190-1,000 nm, more preferably from about 290-500 nm. The glass sheet may be a soda-lime-silica based glass sheet, and/or the corrosion may comprise at least one of sodium carbonate, calcium carbonate, sodium sulfate, and sodium nitrate based corrosion.

In certain example embodiments, a processor may be configured to determine whether or not the glass sheet has significant corrosion thereon based at least on at least a plurality of measured delta ($\Delta$) values from the glass sheet, and based at least on whether more than a predetermined number of the plurality of measured delta ($\Delta$) values exceed the predetermined value and/or are less than the predetermined value.

In certain example embodiments, a processor may be configured to determine whether or not the glass sheet has significant corrosion thereon based at least on a plurality of measured delta ($\Delta$) values from the glass sheet and based on a standard deviation of the plurality of measured delta values.

In certain example embodiments, a processor may be configured to determine whether or not the glass sheet has significant corrosion thereon based at least on a plurality of measured delta ($\Delta$) values from the glass sheet and based on differences in values between the plurality of measured delta values (e.g., based on whether the delta values from the sheet are substantially spread out which indicates corrosion, or whether they are all close together indicating a lack of corrosion). This embodiment may or may not be used in connection with any other embodiment described herein.

DETAILED DESCRIPTION OF EXAMPLE EMBODIMENTS OF THE INVENTION

Sputtering apparatuses, for depositing low-E coatings and other coatings on glass, typically have a washing station that is part of, or works in conjunction with, the sputtering apparatus/system. The washing station is typically located prior to the sputtering chamber(s), for washing off dirt and the like from glass before the glass is coated.

Soda-lime-silica based glass, as well as other glass, is subject to corrosion. Water reacts with soda-lime-silica glass, albeit very slowly. When water (including humidity) is permitted to remain on uncoated soda-lime-silica based glass for long periods of time, corrosion can occur. An example of corrosion may involve an ion exchange process involving alkali or alkaline earth ions from the glass and hydrogen ions from the water. For instance, water leaches, or takes, alkali or alkaline earth (e.g., sodium) ions from soda-lime-silica based float glass. Eventually, the increase in alkalinity of the contact solution on glass may initiate more damaging reactions. For instance, once solution pH levels get to above 9, hydroxide ion concentration is sufficient to begin attack of the silicate network of the glass, with a reaction including severing of silicon-oxygen bonds as the glass slowly begin to dissolve at the surface thereof and microscopic pitting of the surface occurs. The glass network begins to slowly dissolve, and by products such as at least one of sodium carbonate, calcium carbonate, sodium sulfate, sodium nitrate, sodium silicate, and/or calcium silicate work to degrade the appearance of the glass. Another point, these materials could form in: stoichiometric or non-stoichiometric compositions, crystalline or amorphous forms, hydrated or anhydrous, single or multiple components/mixtures. All depending on the glass and the environment the glass corrodes in. This may be referred to as Stage 2 corrosion. If this reaction is allowed to continue, surface damage will become more apparent and the glass may have a significant iridescence or a dense, translucent haze. Carbon dioxide in the atmosphere may also react with moisture on the glass surface, to form surface residue such as sodium carbonate and/or calcium carbonate based corrosion. For example, a way carbonates may form is in absence of water (e.g., when the humidity decreases or goes away or when water evaporates), the byproducts of glass corrosion cannot evaporate with the water so they precipitate out of evaporating water in reaction with carbon dioxide or such in the atmosphere and form carbonates. The same may hold for sulfates (reacting with SOx) or nitrates (NOx). In such a manner, the optical quality of the glass degrades, even though the structural soundness of the glass is maintained. Such corrosion may or may not be visible to the naked eye.

Stage 1 corrosion (e.g., glass surface may interdiffuse and be subject to hydrolysis, which may or may not result in formation of carbonates, sulfates, and/or nitrates, such as with at least one of sodium carbonate, calcium carbonate, sodium sulfate, and sodium nitrate based corrosion) may or may not be visible to the naked eye, but is often not visible to the naked eye. On the other hand, Stage 2 corrosion (e.g., at least one of sodium carbonate, calcium carbonate, sodium sulfate, and sodium nitrate based corrosion) may or may not be visible to the naked eye, but often is visible to the naked eye.

It has been found that when corroded glass is heat treated (e.g., heat bent or thermally tempered) and coated with a low-E coating, the resulting coated article is prone to optical deficiencies such as undesirable transmission, color and/or haze. Thus, it is undesirable for example to coat corroded soda-lime-silica based glass with a low-E coating.

Once glass such as soda-lime-silica glass has significantly corroded, restoring the high surface quality of the glass is difficult. Grinding and/or polishing could work in this respect. However, such solutions are not practical. Thus, once glass become significantly corroded, it may be discarded.

There exists a need for a system/apparatus for reasonably detecting/identifying corrosion on glass such as soda-lime-silica based glass 1. In particular, there is a need to be able to detect/identify such corrosion (e.g., at least one of sodium carbonate, calcium carbonate, sodium sulfate, and sodium nitrate based corrosion, from Stage 1 and/or Stage 2 corrosion) on glass 1 such as soda-lime-silica based glass and other types of glass, so that such glass is not heat treated and/or is not coated with a low-E coating or other type of coating, and/or is not used in other applications where optical appearance is critical.

Figure 1:
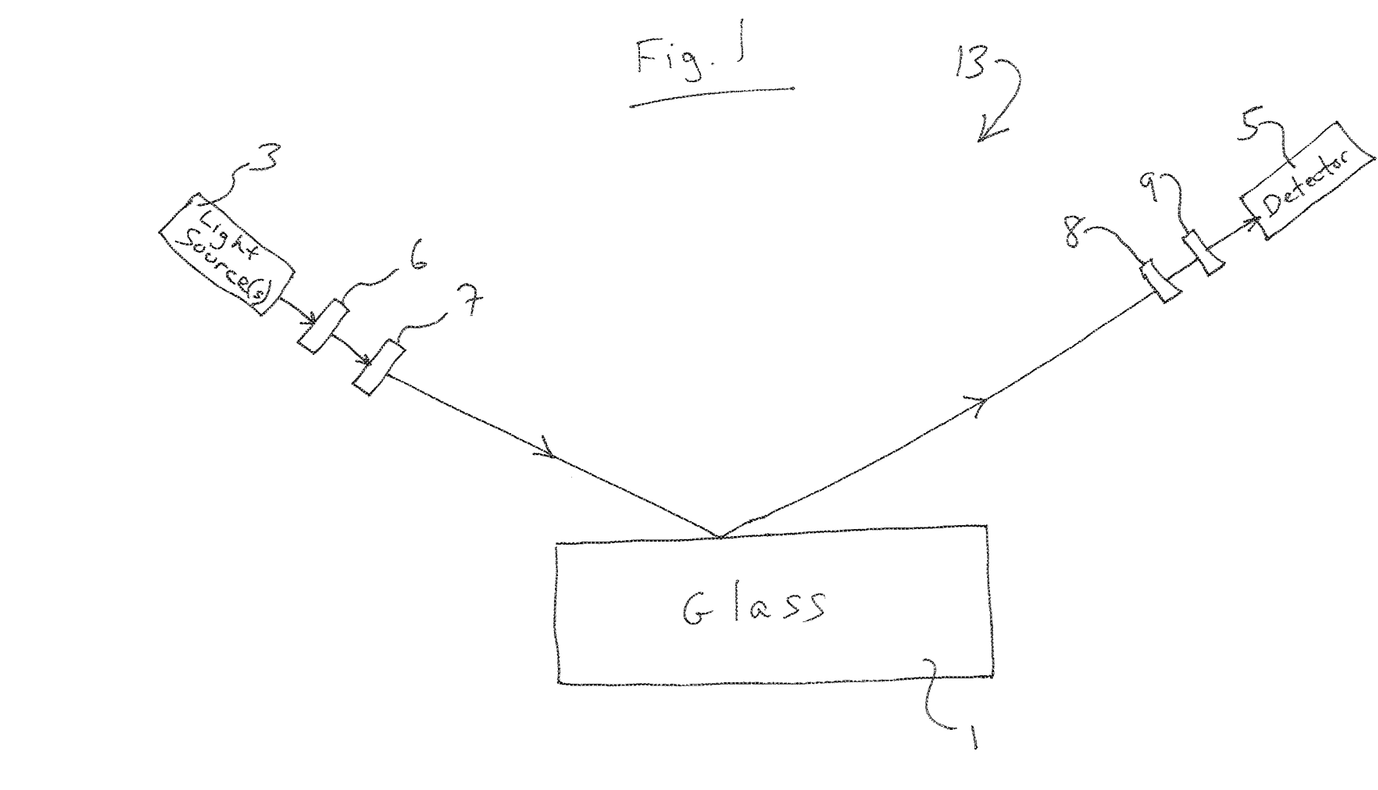
FIG. 1 is a schematic diagram of an apparatus and/or system illustrating ellipsometry being utilized to differentiate between significantly corroded glass and non-corroded glass according to an example embodiment of this invention.
Figure 4A:
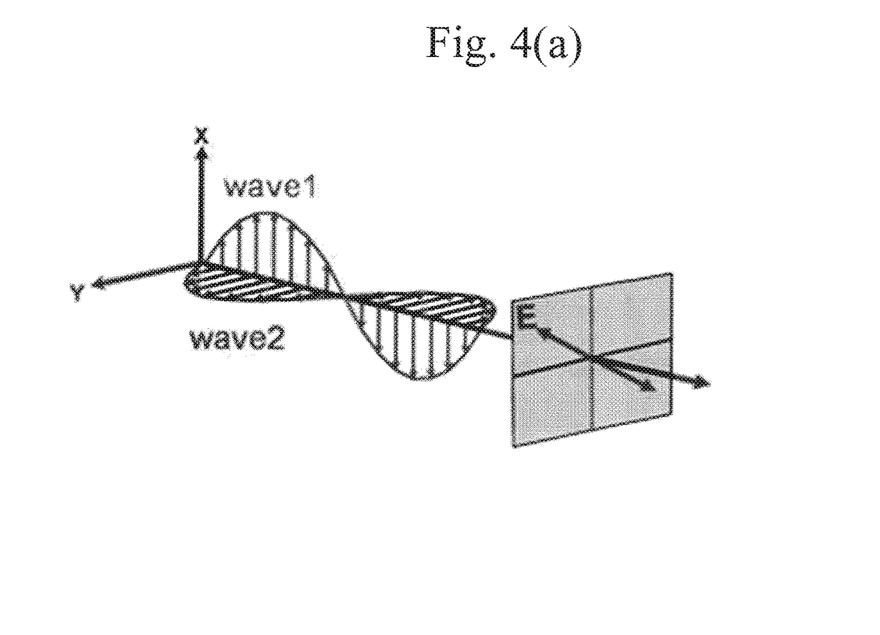
FIGS. 4(a)-4(c) are schematic diagrams illustrating examples of ellipsometry that may be utilized in example embodiments of this invention.
Figure 4B:
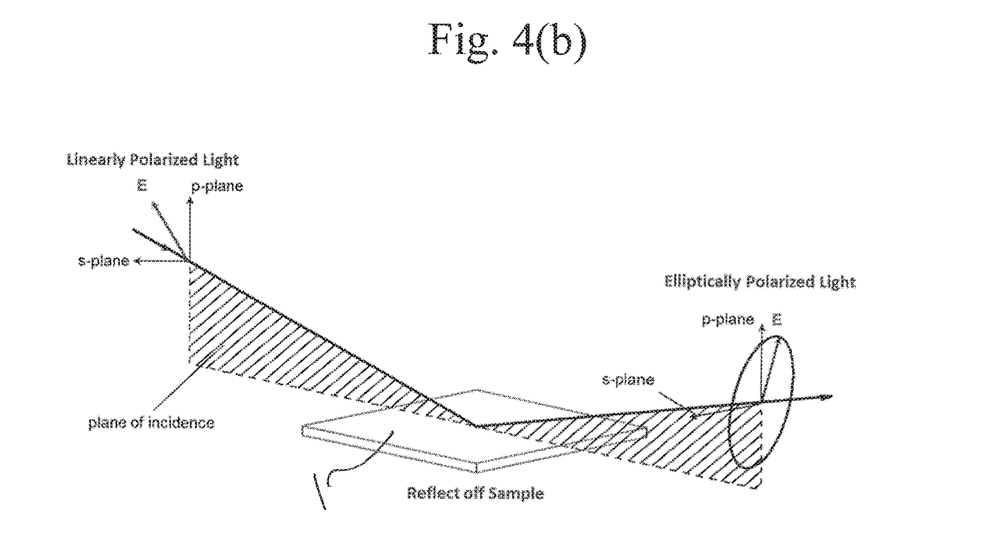
Figure 4C:
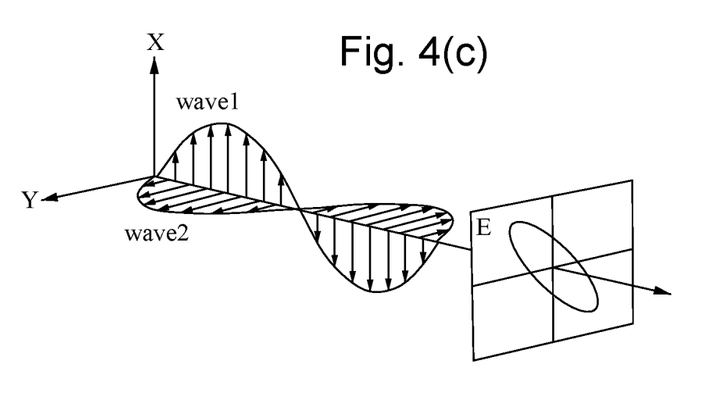
Figure 5:
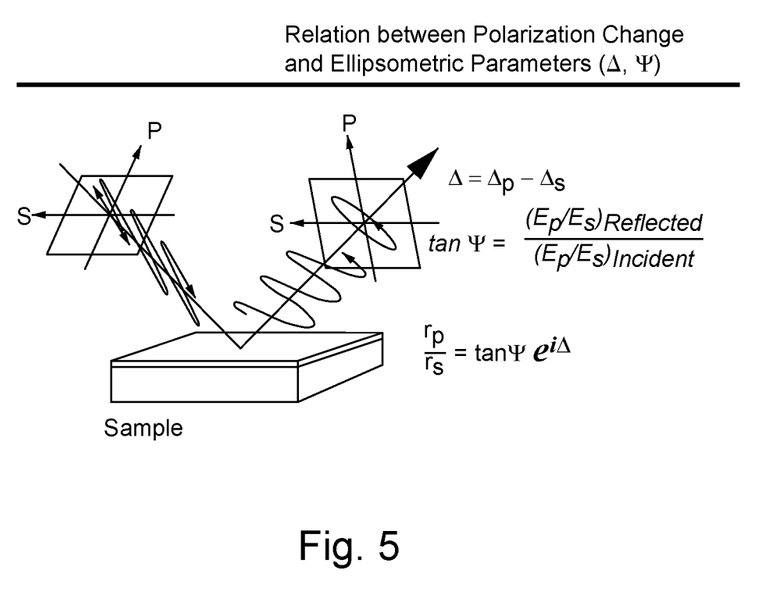
FIG. 5 is a schematic diagrams illustrating relationships between polarization changes and ellipsometric parameters delta (Δ) and Psi (Ψ) that may be utilized in example embodiments of this invention.
Figure 6:
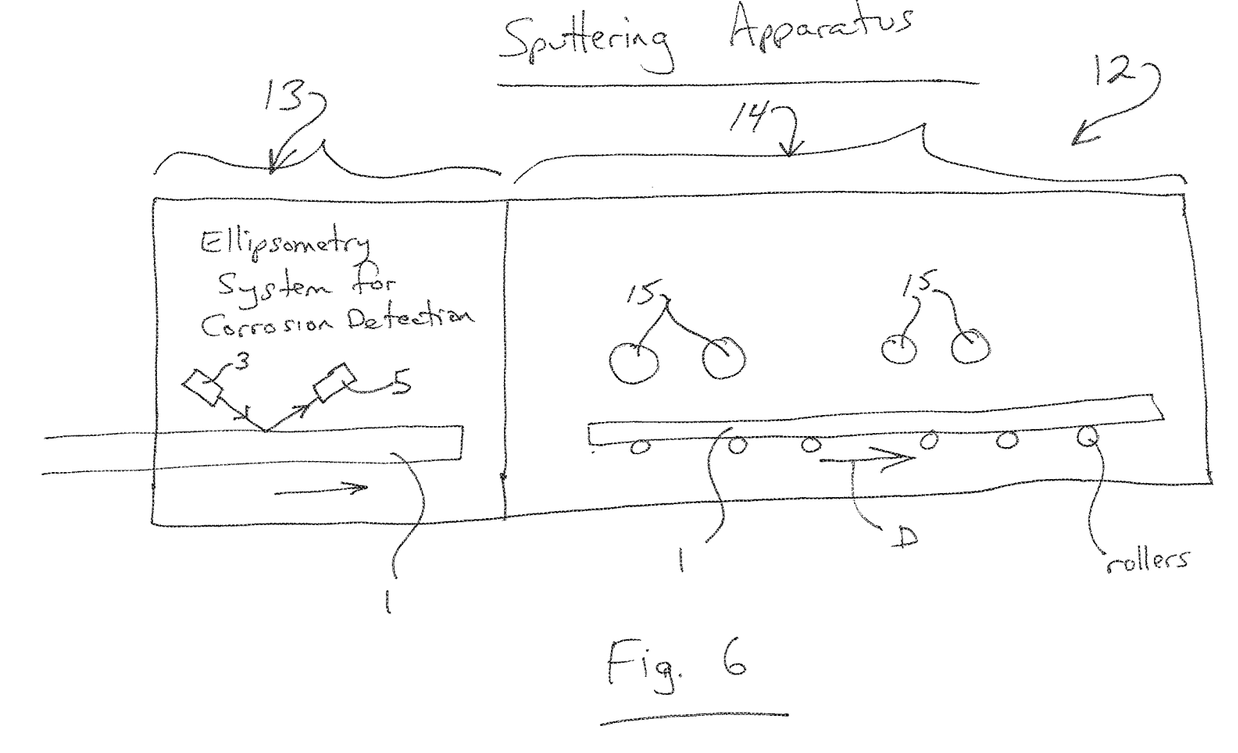
FIG. 6 is a schematic diagram of a sputtering apparatus and/or system illustrating ellipsometry being utilized to differentiate between significantly corroded glass and non-corroded glass prior to sputtering chamber(s) according to an example embodiment of this invention.

Referring to FIGS. 1, 4 and 6 for example, in certain example embodiments of this invention, there is provided a method and/or system utilizing ellipsometry to detect/identify significant corrosion (e.g., at least one of sodium carbonate, calcium carbonate, sodium sulfate, and sodium nitrate based corrosion, from Stage 1 and/or Stage 2 corrosion) on glass sheet 1 such as a soda-lime-silica based glass sheet, so that such significantly corroded glass can be identified and not used in other applications where optical appearance is critical (e.g., heat treatment, coating with low-E or other types of coating, etc.).

In certain example embodiments, spectroscopic ellipsometry is utilized to differentiate between corroded glass and non-corroded glass, so that significantly corroded glass can be detected/identified. The ellipsometry system/apparatus may include electromagnetic radiation being emitted by a light/radiation source(s) 3 (e.g., broad band source) and linearly polarized by a polarizer 6. It may optionally pass through an optional compensator (e.g., retarder, phase modulator, and/or quarter wave plate) 7 and impinge upon glass substrate/sheet 1 to be analyzed. After reflection off the glass sheet 1, the radiation passes through an optional a compensator (e.g., retarder, phase modulator, and/or quarter wave plate) 8 and another polarizer 9 which may be referred to as an analyzer, and then reaches detector 5. Ellipsometry may be a specular optical technique where the angle of incidence on the glass 1 equals or substantially equals the angle of reflection. The incident and the reflected beam span the plane of incidence. Light which is polarized parallel to this plane is p-polarized, and a polarization direction perpendicular or substantially perpendicular is s-polarized.

The measured signal is the change in polarization as the incident radiation (in a known state) interacts with the material structure of interest (reflected, absorbed, scattered, or transmitted). The polarization change is quantified by the amplitude ratio, Ψ, and the phase difference, delta (Δ).

Still referring to FIGS. 1, 4 and 6, ellipsometry measures the complex reflectance ratio of a system, which may be parameterized by the amplitude component Ψ and the phase difference Δ. The polarization state of the light incident upon the glass may be decomposed into an s and a p component.

The s component is oscillating perpendicular or substantially perpendicular to the plane of incidence and parallel to the sample surface, and the p component is oscillating parallel or substantially parallel to the plane of incidence. The amplitudes of the s and p components, after reflection and normalized to their initial value, are denoted by $r_s$ and $r_p$, respectively. Ellipsometry measures the complex reflectance ratio, P (a complex quantity), which is the ratio of $r_p$ over $r_s$:

$$P = r_p/r_s = \tan(\Psi)e^{i\Delta}$$

Thus, $\tan(\Psi)$ is the amplitude ratio upon reflection, and delta ($\Delta$) is the phase shift (difference). Note that the right hand side of the equation is simply another way to represent a complex number. Optionally, angles of P (angle of the linear polarizer), C (wavelength compensator) and A (analyzer) may be obtained and used to determine $\Psi$ and $\Delta$ in a known manner. Standard or generalized ellipsometry may be used. Various different types of ellipsometers may be used for perform the ellipsometry analysis according to various example embodiments of this invention.

In certain example embodiments, the method and/or system using ellipsometry to detect and/or identify corrosion on glass may be part of, or used in conjunction with, a sputtering apparatus 12 that sputter-deposits coatings (e.g., low-E coatings) on glass 1 via sputtering target(s) 15.

FIG. 1 is a schematic diagram of an apparatus and/or system illustrating ellipsometry being utilized to differentiate between significantly corroded glass and non-corroded glass according to an example embodiment of this invention. Radiation from source(s) 3 is incident on glass 1 to be analyzed, and is reflected toward the detector 5, as explained above. The glass may be held or supported, moving or still, on a support such as a platform or rollers, while it is analyzed. As shown in FIG. 6, the ellipsometry apparatus/system 13 of FIG. 1 may be used in or in connection with a sputtering system/apparatus 14, where the ellipsometry system 13 is located prior to the sputtering chamber(s) including the sputtering target(s) 15 where a coating such as a low-E coating is sputter deposited onto the glass substrate 1 that is moving in direction D on the illustrated supporting rollers. Whether or not the glass substrate analyzed by the ellipsometry system 13 is passed to the sputtering system 14 is based on whether significant corrosion is detected on the glass 1 by the ellipsometry system 13. For instance, if the ellipsometry system 13 detects significant corrosion on the glass 1 in FIG. 6, then the glass is discared and is not coated with a low-E coating. On the other hand, if the ellipsometry system 13 does not detect significant corrosion on the glass 1 in FIG. 6, then the glass is passed to a downstream system such as a sputtering system where a low-E coating, or other type of coating, is sputter-deposited onto the glass substrate 1, and/or where heat treatment may be performed. Example low-E coatings are described in U.S. Pat. Nos. 6,936,347, 5,688,585, 5,557,462, 5,425,861, 4,413,877 and 3,682,528, the disclosures of which are all hereby incorporated herein by reference. Glass 1 may be a soda-lime-silica based glass, made via the float process, in certain example embodiments of this invention.

Figure 2:
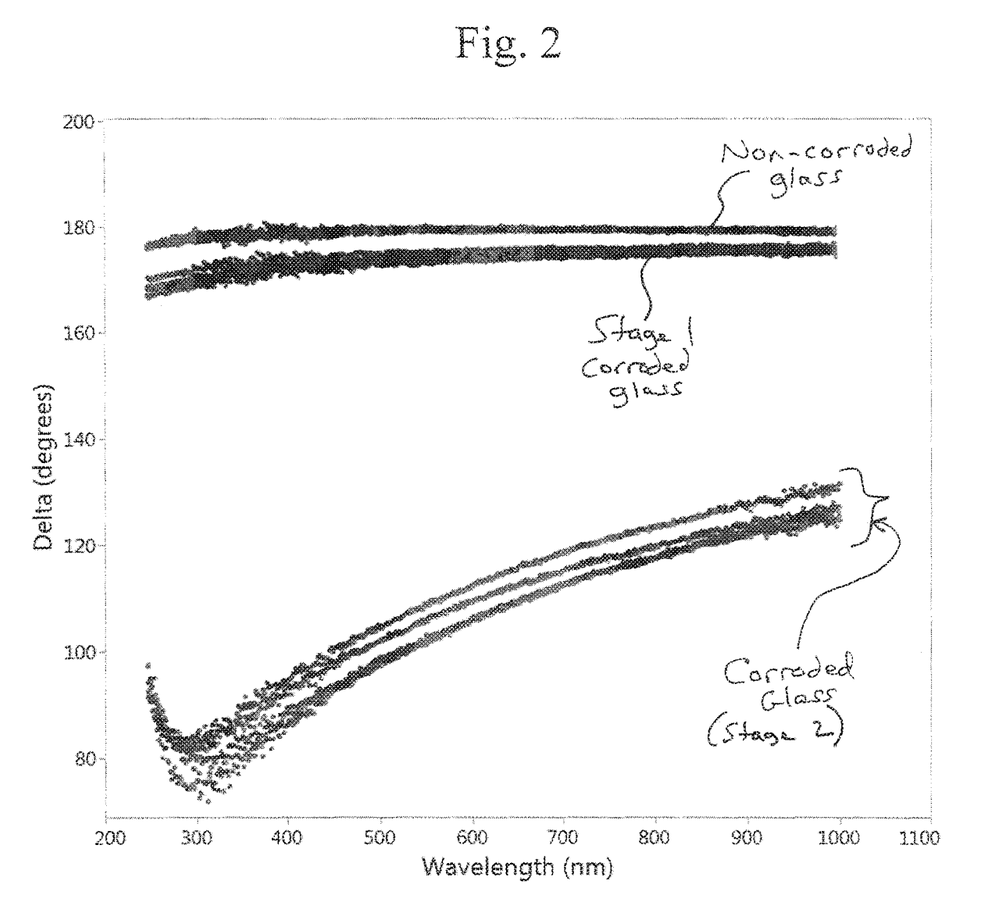
FIG. 2 is a wavelength (nm) vs. delta (degrees) graph illustrating ellipsometry being utilized (from the FIG. 1 and/or FIG. 6 apparatus/system) to differentiate between significantly corroded glass and non-corroded glass according to an example embodiment of this invention.

FIG. 2 is a wavelength (nm) vs. delta ($\Delta$)(degrees) graph illustrating ellipsometry (from the ellipsometry system of FIG. 1 and/or FIG. 6) to differentiate between significantly corroded glass and non-corroded glass according to an example embodiment of this invention. The angle of incidence, of the radiation from the source 3 onto the flat glass sheet 1, may be from about 40-70 degrees, more preferably from about 50-60 degrees, with an example of about 55 degrees for the sample data. The glass samples 1 were less than about 4 mm thick, and were soda-lime-silica based clear float glass. The uppermost plot in FIG. 2, where delta ($\Delta$) values are about 180 degrees, are ellipsometry plots for non-corroded glass for wavelengths from about 250 to 1,000 nm. The middle plots in FIG. 2, where delta ($\Delta$) values are about 170 degrees, are ellipsometry plots for Stage 1 corroded glass for the same wavelengths of from about 250 to 1,000 nm. And the lower plots in FIG. 2, where delta ($\Delta$) values are less than about 140 degrees, are ellipsometry plots for Stage 2 corroded glass for the same wavelengths of from about 250 to 1,000 nm. Thus, the ellipsometry can differentiate between Stage 2 corroded glass, Stage 1 corroded glass, and non-corroded glass.

As shown in FIG. 2, the significantly corroded glass samples had lower delta ($\Delta$) values than did the non-corroded glass samples. Accordingly, the ellipsometry system may determine/detect/identify whether or not an analyzed glass 1 sample is significantly corroded or not based on at least its delta ($\Delta$) value(s), with higher delta ($\Delta$) values indicating a lack of significant corrosion and lower delta ($\Delta$) values indicating significant corrosion. One or a plurality of delta values may be measured for each glass sheet 1. For example, the ellipsometry system 13 may determine/detect/identify whether or not an analyzed glass 1 sample is significantly corroded or not based at least one whether its delta ($\Delta$) value is above a predetermined value (e.g., 175 degrees, 170 degrees, 140 degrees, 130 degrees, or some other predetermined suitable delta ($\Delta$) value chosen based on a degree of corrosion sought to be avoided) for at least one wavelength in a range of from about 250-1000 nm, more preferably for at least one wavelength in a range of from about 290-700 nm, and possibly for at least one wavelength in a range of from about 290-500 nm, with an example being at least one wavelength from about 295-305 nm). If the detected/measured delta ($\Delta$) value(s) is determined by a processor of the detector 5 or detection system to be above the predetermined value, then the analyzed glass 1 is considered not significantly corroded (a small degree of corrosion is permissible in certain instances) and is passed along for sputter-deposition of a low-E or other coating onto the glass 1 and/or for optional heat treatment. However, if the detected/measured delta ($\Delta$) value(s) is determined by a processor of the detector 5 or detection system to be below, or no greater than, the predetermined value, then the analyzed glass 1 is considered significantly corroded (e.g., at least one of sodium carbonate, calcium carbonate, sodium sulfate, and sodium nitrate based corrosion, from Stage 1 and/or Stage 2 corrosion on the glass 1) and for example may be discarded so that it is not passed along for sputter-deposition of the low-E or other coating onto the glass 1.

Figure 3:
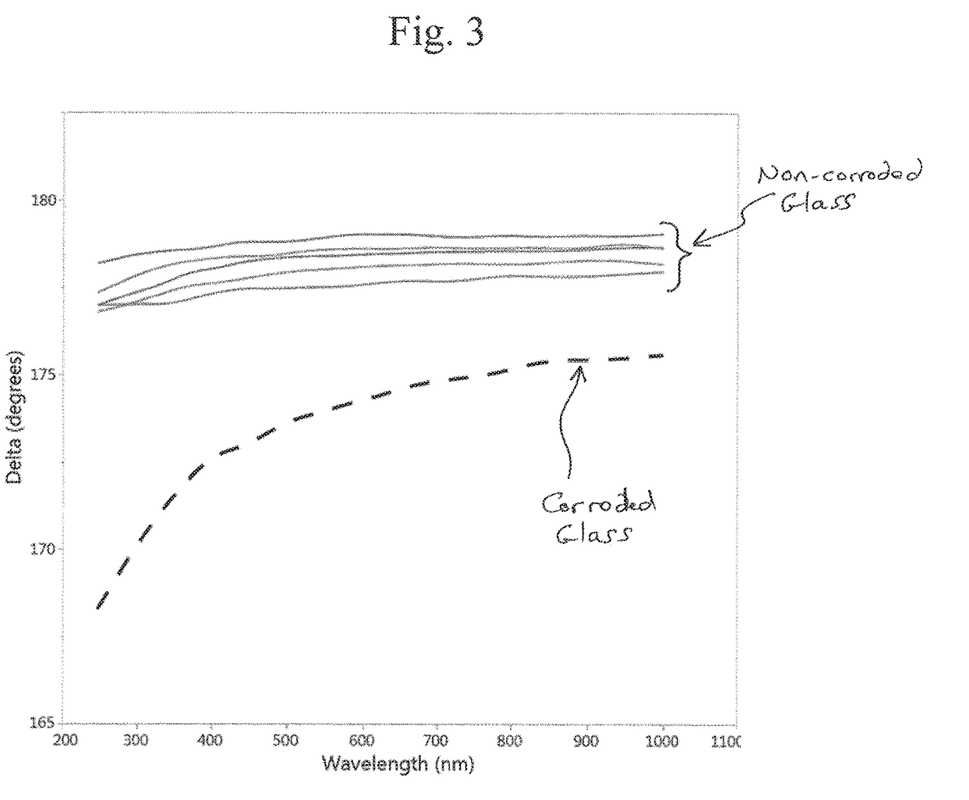
FIG. 3 is a wavelength (nm) vs. delta (degrees) graph illustrating ellipsometry being utilized (from the FIG. 1 and/or FIG. 6 apparatus/system) to differentiate between significantly corroded glass and non-corroded glass according to an example embodiment of this invention.

FIG. 3 is a wavelength (nm) vs. delta ($\Delta$)(degrees) graph illustrating ellipsometry (from the ellipsometry system of FIG. 1 and/or FIG. 6) to differentiate between significantly corroded glass and non-corroded glass according to an example embodiment of this invention. The angle of incidence, of the radiation from the source 3 onto the glass 1, may be from about 40-70 degrees, more preferably from about 50-60 degrees, with an example of about 55 degrees for the sample data. The glass samples 1 were less than about 4 mm thick, and were soda-lime-silica based clear float glass. The upper plots in FIG. 3, where delta ($\Delta$) is from about 177-179 degrees, are ellipsometry plots for non-corroded glass for wavelengths ($\lambda$) from about 250 to 1,000 nm. On the other hand, the lower dotted line plot in FIG. 3, where delta (Δ) is mostly less than about 175 degrees, is an ellipsometry plot for significantly corroded glass for the same wavelengths of from about 250 to 1,000 nm. Thus, the ellipsometry can differentiate between the significantly corroded glass (dotted line in FIG. 3), and the non-corroded glass (upper plots in FIG. 3). As shown in FIG. 3, the significantly corroded glass samples had lower delta (Δ) values than did the non-corroded glass sample. Accordingly, the ellipsometry system may determine/detect/identify whether or not an analyzed glass 1 sample is significantly corroded or not based on at least its delta (Δ) value(s), with higher delta (Δ) values indicating a lack of significant corrosion and lower delta (Δ) values indicating significant corrosion. For example, the ellipsometry system 13 may determine/detect/identify whether or not an analyzed glass 1 sample is significantly corroded or not based at least one whether its delta (Δ) value(s) is above a predetermined value (e.g., 175 degrees, 170 degrees, or some other Δ value chosen based on a degree of corrosion sought to be avoided) for at least one wavelength in a range of from about 250-1000 nm, more preferably for at least one wavelength in a range of from about 290-700 nm, and possibly for at least one wavelength in a range of from about 290-500 nm, with an example being for at least one wavelength in a range of from about 295-305 nm). If the detected/measured delta (Δ) value(s) is determined by a processor of the detector 5 or detection system to be above the predetermined value, then the analyzed glass 1 is considered not significantly corroded (a small degree of corrosion is permissible in certain instances) and is passed along for sputter-deposition of the low-E coating, or other type of coating, onto the glass 1. However, if the detected/measured delta (Δ) value(s) is determined by a processor of the detector 5 or detection system to be below, or no greater than, the predetermined value, then the analyzed glass 1 is considered significantly corroded and is discarded so that it is not passed along for sputter-deposition of the low-E or other coating onto the glass 1.

In certain example embodiments, the processor of the ellipsometry system is configured to determine whether or not the glass sheet has significant corrosion thereon based at least on a plurality of measured delta (Δ) values from the glass sheet, and based at least on whether more than a predetermined number of the plurality of measured delta (Δ) values exceed the predetermined value and/or are less than the predetermined value.

In certain example embodiments, the processor of the ellipsometry system is configured to determine whether or not the glass sheet has significant corrosion thereon based at least on a plurality of measured delta (Δ) values from the glass sheet and based on a standard deviation of the plurality of measured delta values. In other words, the processor of the ellipsometry system is configured to determine whether or not the glass sheet has significant corrosion thereon based at least on a plurality of measured delta (Δ) values from the glass sheet and based on differences in values between the plurality of measured delta values, and/or how spread out the plurality of delta (Δ) values are. For instance, assume that ten delta (Δ) values are measured from a given glass sheet 1. The less spread out the delta (Δ) values are, the less likely that there is corrosion on the glass. The more spread out the delta (Δ) values are, the more likely there is corrosion on the glass. Thus, if the standard deviation of the plurality of delta (Δ) values taken from different locations on the glass sheet 1 is less than a predetermined value (e.g., 1.5 or 2.0), then the system may determine that there is no significant corrosion on the measured surface of the glass sheet. On the other hand, if the standard deviation of the plurality of delta (Δ) values taken from different locations on the glass sheet 1 is greater than (or at least as high as) a predetermined value (e.g., 1.5 or 2.0), then the system may determine that there is significant corrosion on the measured surface of the glass sheet.

Instead of using standard deviation of the plurality of measured delta (Δ) values taken from different locations on the glass sheet 1, other techniques based on the differences between a plurality of the values may instead be used. For example, if the difference between a plurality of delta (Δ) values taken from different locations on the glass sheet 1 is less than a predetermined value (e.g., 1.5 or 2.0), then the system may determine that there is no significant corrosion on the measured surface of the glass sheet. On the other hand, if the difference between the plurality of delta (Δ) values (all of the measured values, or between only a select few of the different values, or between the largest and smallest of the values) taken from different locations on the glass sheet 1 is greater than (or at least as high as) a predetermined value (e.g., 1.5 or 2.0), indicating a large spread between the measured delta values, then the system may determine that there is significant corrosion on the measured surface of the glass sheet.

In an example embodiment of this invention, there is provided a method of making a coated glass sheet, the method comprising: analyzing an uncoated glass sheet via ellipsometry analysis, including directing radiation toward the uncoated glass sheet so as to be reflected by the uncoated glass sheet; determining (e.g., by at least one processor of a ellipsometry system) whether or not the uncoated glass sheet has significant corrosion thereon based on the ellipsometry analysis; and selectively allowing the uncoated glass sheet to be coated with a low-E coating based at least on whether significant corrosion is determined to be on the uncoated glass sheet. The determining may comprise determining whether or not the uncoated glass sheet has significant corrosion thereon based at least on a measured delta (Δ) value, wherein the measured delta (Δ) value is based on at least a polarization change between the radiation incident on the uncoated glass sheet and the radiation reflected by the uncoated glass sheet. The determining may comprise determining whether or not the uncoated glass sheet has significant corrosion thereon based at least on whether the measured delta (Δ) value exceeds a predetermined value, so that it is determined that the uncoated glass sheet is not significantly corroded when the measured delta (Δ) value exceeds the predetermined value, and it is determined that the uncoated glass sheet is significantly corroded when the measured delta (Δ) value does not exceed the predetermined value. The measured delta (Δ) value may comprise at least one delta (Δ) value measured for at least one wavelength from about 250-1,000 nm, more preferably from about 290-500 nm. The glass sheet may be a soda-lime-silica based glass sheet, and/or the corrosion may comprise at least one of sodium carbonate, calcium carbonate, sodium sulfate, and sodium nitrate based corrosion.

In an example embodiment of this invention, there is provided a system for detecting corrosion on glass, the system comprising: a support for supporting a glass sheet; a ellipsometry system for analyzing the glass sheet, the ellipsometry system including at least one radiation source and a processor, wherein the at least one radiation source is configured to direct radiation toward the glass sheet so as to be reflected by the glass sheet; and wherein the processor of the ellipsometry system is configured to determine whether or not the glass sheet has significant corrosion thereon.

In the system of the immediately preceding paragraph, the processor of the ellipsometry system may be configured to determine whether or not the glass sheet has significant corrosion thereon based at least on a measured delta (Δ) value, wherein the measured delta (Δ) value is based on at least a polarization change between the radiation incident on the glass sheet and the radiation reflected by the glass sheet.

In the system of the any of the preceding two paragraphs, the processor of the ellipsometry system may be configured to determine whether or not the glass sheet has significant corrosion thereon based at least on whether the measured delta (Δ) value exceeds a predetermined value, so that the processor is configured to determine that the glass sheet is not significantly corroded when the measured delta (Δ) value exceeds the predetermined value, and is configured to determine that the glass sheet is significantly corroded when the measured delta (Δ) value does not exceed the predetermined value.

In the system of any of the preceding three paragraphs, the measured delta (Δ) value may comprise at least one delta (Δ) value measured for at least one wavelength from about 190-1,000 nm, more preferably from about 250-1,000 nm, more preferably from about 290-500 nm, and possibly from about 290-305 nm.

In the system of any of the preceding four paragraphs, the glass sheet may be a soda-lime-silica based glass sheet, and/or may be uncoated.

In the system of any of the preceding five paragraphs, the ellipsometry system may further comprise a polarizer configured to be located between at least the radiation source and the glass sheet.

In the system of any of the preceding six paragraphs, the processor may further be configured to selectively allow the glass sheet to be coated with a low-E coating by a sputtering system, including at least one sputtering target, based at least on whether significant corrosion is detected on the glass sheet.

In the system of any of the preceding seven paragraphs, the processor of the ellipsometry system may be configured to determine whether or not the glass sheet has significant corrosion thereon based at least on whether a plurality of measured delta (Δ) values from the glass sheet exceed a predetermined value; so that the processor may be configured to determine that the glass sheet is not significantly corroded when the plurality of measured delta (Δ) values exceed the predetermined value, and/or may be configured to determine that the glass sheet is significantly corroded when the plurality of measured delta (Δ) values do not exceed the predetermined value.

In the system of any of the preceding eight paragraphs, the processor of the ellipsometry system may be configured to determine whether or not the glass sheet has significant corrosion thereon based at least on a plurality of measured delta (Δ) values from the glass sheet, and based at least on whether more than a predetermined number of the plurality of measured delta (Δ) values exceed the predetermined value and/or are less than the predetermined value.

In the system of any of the preceding nine paragraphs, the processor of the ellipsometry system may be configured to determine whether or not the glass sheet has significant corrosion thereon based at least on a plurality of measured delta (Δ) values from the glass sheet and based on a standard deviation of the plurality of measured delta values, where the measured delta (Δ) values are based on at least a polarization change between the radiation incident on the glass sheet and the radiation reflected by the glass sheet.

In the system of any of the preceding ten paragraphs, the processor of the ellipsometry system may be configured to determine whether or not the glass sheet has significant corrosion thereon based at least on a plurality of measured delta (Δ) values from the glass sheet and based on differences in values of the plurality of measured delta values, where the measured delta (Δ) values are based on at least a polarization change between the radiation incident on the glass sheet and the radiation reflected by the glass sheet.

While ellipsometry is used in preferred embodiments of this invention to detect surface corrosion on glass, it is possible that other types of analysis may instead be used that are based on phase shifts and/or differences in measured polarizations between incident and exiting radiation.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. A system for detecting corrosion on glass, the system comprising:
    a support for supporting a glass sheet;
    an ellipsometry system for analyzing the glass sheet, the ellipsometry system including at least one radiation source and a processor, wherein the at least one radiation source is configured to direct radiation toward the glass sheet so as to be reflected by the glass sheet;
    wherein the processor of the ellipsometry system is configured to determine whether or not the glass sheet has significant corrosion thereon based on at least the radiation reflected by the glass sheet; and
    wherein the processor is configured to determine whether or not the glass sheet has significant corrosion thereon based at least on a plurality of measured delta (Δ) values from the glass sheet and based on differences in values between the plurality of measured delta values, where the measured delta (Δ) values are based on at least a polarization change between the radiation incident on the glass sheet and the radiation reflected by the glass sheet.

2. The system of claim 1, wherein the processor of the ellipsometry system is configured to determine whether or not the glass sheet has significant corrosion thereon based at least on whether at least one of the measured delta (Δ) values exceeds a predetermined value, so that the processor is configured to determine that the glass sheet is not significantly corroded when the measured delta (Δ) value exceeds the predetermined value, and is configured to determine that the glass sheet is significantly corroded when the measured delta (Δ) value does not exceed the predetermined value.

3. The system of claim 2, wherein the measured delta (Δ) value comprises at least one delta (Δ) value measured for at least one wavelength from about 190-1,000 nm.

4. The system of claim 2, wherein the measured delta (Δ) value comprises at least one delta (Δ) value measured for at least one wavelength from about 290-500 nm.

5. The system of claim 2, wherein the measured delta (Δ) value comprises at least one delta (Δ) value measured for at least one wavelength from about 290-305 nm.

6. The system of claim 1, wherein the glass sheet is a soda-lime-silica based glass sheet.

7. The system of claim 1, wherein the glass sheet is uncoated.

8. The system of claim 1, wherein the ellipsometry system further comprises a polarizer configured to be located between at least the radiation source and the glass sheet.

9. A system for detecting corrosion on glass, the system comprising:
a support for supporting a glass sheet;
an ellipsometry system for analyzing the glass sheet, the ellipsometry system including at least one radiation source and a processor, wherein the at least one radiation source is configured to direct radiation toward the glass sheet so as to be reflected by the glass sheet;
wherein the processor of the ellipsometry system is configured to determine whether or not the glass sheet has significant corrosion thereon based on at least the radiation reflected by the glass sheet; and
wherein the processor is further configured to selectively allow the glass sheet to be coated with a low-E coating based at least on whether significant corrosion is detected on the glass sheet.

10. The system of claim 1, wherein the processor of the ellipsometry system is configured to determine whether or not the glass sheet has significant corrosion thereon based at least on whether the plurality of measured delta ($\Delta$) values from the glass sheet exceed a predetermined value;
so that the processor is configured to determine that the glass sheet is not significantly corroded when the plurality of measured delta ($\Delta$) values exceed the predetermined value, and/or is configured to determine that the glass sheet is significantly corroded when the plurality of measured delta ($\Delta$) values do not exceed the predetermined value.

11. The system of claim 1, wherein the processor of the ellipsometry system is configured to determine whether or not the glass sheet has significant corrosion thereon based at least on the plurality of measured delta ($\Delta$) values from the glass sheet, and based at least on whether more than a predetermined number of the plurality of measured delta ($\Delta$) values exceed the predetermined value and/or are less than the predetermined value.

12. The system of claim 1, wherein the processor of the ellipsometry system is configured to determine whether or not the glass sheet has significant corrosion thereon based at least on the plurality of measured delta ($\Delta$) values from the glass sheet and based on a standard deviation of the plurality of measured delta values.

13. The system of claim 9, wherein the processor of the ellipsometry system is configured to determine whether or not the glass sheet has significant corrosion thereon based at least on a plurality of measured delta ($\Delta$) values from the glass sheet and based on differences in values between the plurality of measured delta values, where the measured delta ($\Delta$) values are based on at least a polarization change between the radiation incident on the glass sheet and the radiation reflected by the glass sheet.

14. A sputtering system comprising the system of claim 1, and at least one sputtering chamber including at least one sputtering target configured to selectively sputter-deposit a low-E coating onto the glass sheet depending on whether or not significant corrosion is detected on the glass sheet, wherein a sputtering system including the at least one sputtering chamber and the at least one sputtering target is configured to selectively sputter-depositing a low-E coating on the glass sheet based at least on whether significant corrosion is determined to be on the uncoated glass sheet.

15. A method for detecting corrosion on glass, the method comprising:
analyzing a glass sheet via ellipsometry analysis, including directing radiation toward the glass sheet so as to be reflected by the glass sheet; and
determining whether or not the glass sheet has significant corrosion thereon based on the ellipsometry analysis, including determining whether or not the glass sheet has significant corrosion thereon based at least on a plurality of measured delta ($\Delta$) values from the glass sheet and based on differences in values between the plurality of measured delta ($\Delta$) values, where the measured delta ($\Delta$) values are based on at least a polarization change between the radiation incident on the glass sheet and the radiation reflected by the glass sheet.

16. The method of claim 15, wherein the determining further comprises determining whether or not the glass sheet has significant corrosion thereon based at least on whether at least one of the measured delta ($\Delta$) values exceeds a predetermined value, so that it is determined that the glass sheet is not significantly corroded when the measured delta ($\Delta$) value exceeds the predetermined value, and it is determined that the glass sheet is significantly corroded when the measured delta ($\Delta$) value does not exceed the predetermined value.

17. The method of claim 16, wherein the measured delta ($\Delta$) value comprises at least one delta ($\Delta$) value measured for at least one wavelength from about 250-1,000 nm.

18. The method of claim 16, wherein the measured delta ($\Delta$) value comprises at least one delta ($\Delta$) value measured for at least one wavelength from about 290-500 nm.

19. The method of claim 16, wherein the measured delta ($\Delta$) value comprises at least one delta ($\Delta$) value measured for at least one wavelength from about 290-305 nm.

20. The method of claim 15, wherein the glass sheet is a soda-lime-silica based glass sheet.

21. The method of claim 15, wherein the glass sheet is uncoated.

22. The method of claim 15, further comprising selectively allowing the glass sheet to be coated with a low-E coating based at least on whether significant corrosion is detected on the glass sheet.

23. The method of claim 15, wherein the determining comprises determining whether or not the glass sheet has significant corrosion thereon based at least on whether the plurality of measured delta ($\Delta$) values from the glass sheet exceed a predetermined value.

24. The method of claim 23, wherein the determining comprises determining that the glass sheet is not significantly corroded when the plurality of measured delta ($\Delta$) values exceed the predetermined value, and/or determining that the glass sheet is significantly corroded when the plurality of measured delta ($\Delta$) values do not exceed the predetermined value.

25. The method of claim 15, wherein the determining comprises determining whether or not the glass sheet has significant corrosion thereon based at least on a standard deviation of the plurality of measured delta values.

26. The method of claim 15, wherein the determining comprises determining whether or not the glass sheet has significant corrosion thereon based at least on differences in values of the plurality of measured delta values.

27. A method of making a coated glass sheet, the method comprising:
analyzing an uncoated glass sheet via ellipsometry analysis, including directing radiation toward the uncoated glass sheet so as to be reflected by the uncoated glass sheet;

determining whether or not the uncoated glass sheet has significant corrosion thereon based on the ellipsometry analysis; and selectively allowing the uncoated glass sheet to be coated with a low-E coating based at least on whether significant corrosion is determined to be on the uncoated glass sheet.

28. The method of claim 27, wherein the determining comprises determining whether or not the uncoated glass sheet has significant corrosion thereon based at least on a measured delta ($\Delta$) value, wherein the measured delta ($\Delta$) value is based on at least a polarization change between the radiation incident on the uncoated glass sheet and the radiation reflected by the uncoated glass sheet.

29. The method of claim 27, wherein the glass sheet is a soda-lime-silica based glass sheet.

30. The method of claim 28, wherein the corrosion comprises at least one of sodium carbonate, calcium carbonate, sodium sulfate, and sodium nitrate based corrosion.

* * * * *